(12) United States Patent
Shaw et al.

(10) Patent No.: US 10,617,831 B2
(45) Date of Patent: Apr. 14, 2020

(54) FRONTAL ATTACHMENT FOR DENTAL SYRINGE WITH OBLIQUE NEEDLE ADVANCEMENT AND RETRACTION

(71) Applicants: Retractable Technologies, Inc., Little Elm, TX (US); Thomas J. Shaw, Frisco, TX (US)

(72) Inventors: Thomas J. Shaw, Frisco, TX (US); Mark Small, Heavener, OK (US)

(73) Assignee: Retractable Technologies, Inc., Little Elm, TX (US)

( * ) Notice: Subject to any disclaimer, the term of this patent is extended or adjusted under 35 U.S.C. 154(b) by 410 days.

(21) Appl. No.: 15/797,713

(22) Filed: Oct. 30, 2017

(65) Prior Publication Data

US 2019/0125980 A1 May 2, 2019

(51) Int. Cl.
*A61M 5/32* (2006.01)
*A61M 5/34* (2006.01)
*A61M 5/24* (2006.01)
*A61M 19/00* (2006.01)

(52) U.S. Cl.
CPC ........ *A61M 5/3245* (2013.01); *A61M 5/2466* (2013.01); *A61M 5/321* (2013.01); *A61M 5/3232* (2013.01); *A61M 5/34* (2013.01); *A61M 5/345* (2013.01); *A61M 19/00* (2013.01); *A61M 2005/2407* (2013.01); *A61M 2005/2474* (2013.01); *A61M 2210/0625* (2013.01)

(58) Field of Classification Search
CPC ................ A61M 5/3245; A61M 5/345; A61M 2005/341; A61M 2005/2407; A61M 5/2466; A61M 5/34; A61M 5/3202; A61M 5/322; A61M 5/321; A61M 5/3219; A61M 5/3232; A61M 2005/3117; A61M 2005/3118; A61M 2005/312
See application file for complete search history.

(56) References Cited

U.S. PATENT DOCUMENTS

| 5,248,303 | A | * | 9/1993 | Margolin | ............ | A61M 5/3232 128/919 |
| 5,263,942 | A | * | 11/1993 | Smedley | ............... | A61M 5/322 604/110 |
| 5,298,023 | A | * | 3/1994 | Haber | ................. | A61M 5/2448 604/191 |
| 5,300,038 | A | * | 4/1994 | Haber | ................... | A61M 5/322 604/187 |
| 5,498,245 | A | * | 3/1996 | Whisson | ............... | A61M 5/322 604/198 |

(Continued)

*Primary Examiner* — Jenna Zhang
(74) *Attorney, Agent, or Firm* — Ross Barnes LLP; Monty L. Ross

(57) ABSTRACT

A frontal attachment for a conventional aspirating dental syringe comprising a barrel connector housing releasably attachable to the front end of the barrel of an aspirating dental syringe, an injection needle guide attached to the barrel connector housing, an injection needle attached to and supported by a needle holder assembly reciprocatably disposed in a needle guide slot between the injection needle guide and the barrel connector housing in oblique relation to the longitudinal axis of the aspirating dental syringe, and a second needle projecting rearwardly from the barrel connector housing to establish fluid communication with a carpule disposed in the conventional aspirating dental syringe.

14 Claims, 7 Drawing Sheets

(56) References Cited

U.S. PATENT DOCUMENTS

| | | | |
|---|---|---|---|
| 5,585,651 A * | 12/1996 | Kitagawa | H01L 29/7394 257/135 |
| 5,997,512 A | 12/1999 | Shaw | |
| 6,221,055 B1 | 4/2001 | Shaw et al. | |
| 2010/0317999 A1 * | 12/2010 | Shaw | A61B 5/150389 600/576 |
| 2014/0012206 A1 * | 1/2014 | Shaw | A61M 5/3221 604/198 |
| 2014/0221968 A1 * | 8/2014 | Ransbury | A61M 39/06 604/506 |

\* cited by examiner

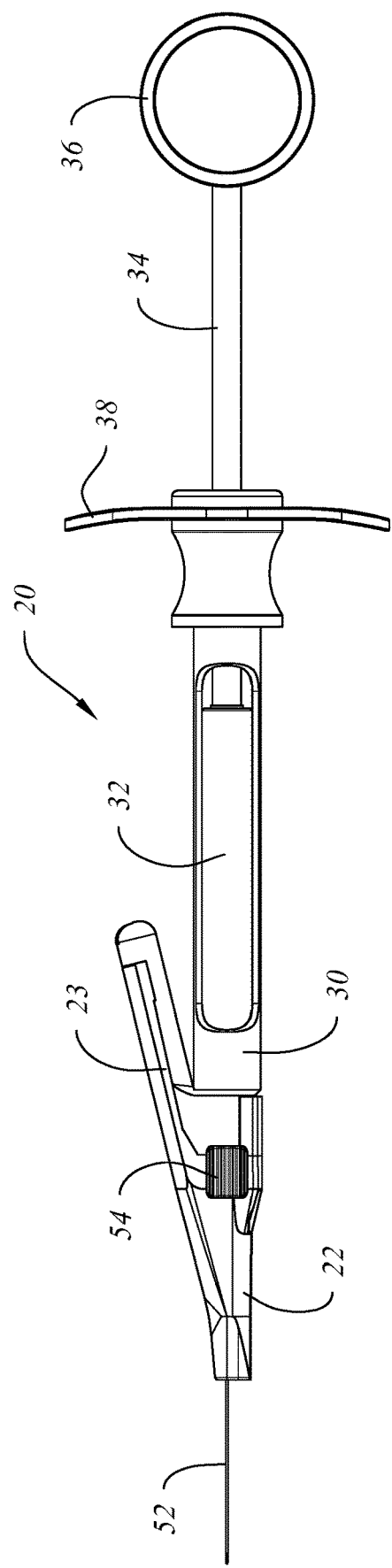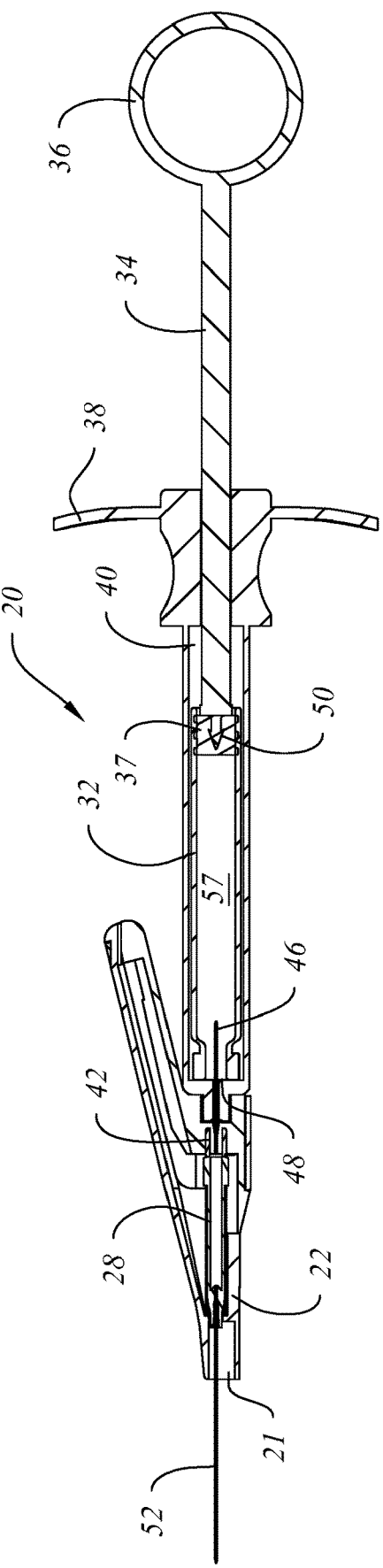
FIG. 7
FIG. 8

FRONTAL ATTACHMENT FOR DENTAL SYRINGE WITH OBLIQUE NEEDLE ADVANCEMENT AND RETRACTION

FIELD OF THE INVENTION

This invention relates to a disposable frontal attachment configured for use with a conventional aspirated dental syringe of the type used for repeatedly injecting small doses of a liquid medicament, typically a local anesthetic administered by a dentist to a patient at different times and/or injection sites prior to and during a dental procedure. More particularly, the frontal attachment is releasably attachable to the front of a conventional dental syringe and further comprises a rearwardly biased injection needle supported by a needle holder and a needle guide that are disposed in oblique relation to the central axis of the dental syringe before and between successive uses during a single procedure. Prior to each sequential injection during the procedure, the injection needle is advanced forwardly by applying digital pressure to a touch surface of the guide until the injection needle is moved into a forwardly projecting position where coaxial alignment with the dental syringe during use. As the injection needle is advanced into coaxial alignment with the dental syringe, a coiled spring surrounding the needle and needle holder is compressed and urges the rearwardly facing end of the needle holder into contact with an annular seal, thereby reducing the likelihood of fluid leakage during use. Between uses, or at the conclusion of the procedure, the injection needle is withdrawn back inside the frontal attachment by a gentle application of digital pressure applied obliquely to the touch pad in cooperation with the spring force exerted by the compressed coil spring as it expands. The frontal attachment can then be detached from the syringe (as by unthreading) at the conclusion of the procedure and safely deposited in a suitable trash receptacle.

DESCRIPTION OF RELATED ART

Conventional dental syringes are often referred to as "aspirating syringes" and frequently comprise a thumb ring that a dentist can use to withdraw the plunger slightly to determine whether the injection needle tip is disposed inside a blood vessel (as distinguished from inside tissue) prior to injecting an anesthetic. If the injection needle tip is inside a blood vessel, a minor amount of blood will be aspirated when the plunger is moved rearwardly, thereby providing a visual indicator that the needle tip should be repositioned prior to further use. Aspirating syringes are often made with metal components and usually comprise a barrel with opposed finger flanges, a thumb ring, and a threaded front tip where a needle holder supporting an injection needle releasably attaches to the barrel. A carpule containing a liquid anesthetic is inserted into the device through a slot in the side of the barrel. Forward pressure applied to a plunger configured as a piston rod with a harpoon disposed on the front end causes the harpoon to engage and embed in a rubber stopper at the rear of the carpule when the plunger is initially advance toward the carpule. Once the harpoon engages the rubber stopper, the dentist can apply forward pressure on the plunger to insert the injection needle into a patient, can apply rearward pressure on the plunger to aspirate once the needle is in inserted, and can again apply forward pressure on the plunger to inject a desired amount of anesthetic into the patient.

Conventional needles used in conjunction with dental syringes are typically double-ended, meaning that they have one forwardly facing and one rearwardly facing needle tip, with a metal or plastic hub disposed between the two needle tips that can be releasably secured (such as by threading) to the front end of the syringe barrel. Protective needle caps are desirably provided at each end to reduce the likelihood of contamination prior to use. The rearwardly facing needle tip is desirably long enough to penetrate an elastomeric septum at the front end of the carpule when oriented as it is installed inside a dental syringe barrel to provide fluid communication between the inside of the carpule and the injection needle tip. Dental needles come in various lengths and gauges, and the forwardly extending needle tip of the injection needle is desirably long enough for the intended use. For example, needles used by dentists for mandibular injections are typically longer than those used for maxillary injections. Once the elastomeric septum is punctured by a rearwardly facing needle, the medicament can flow forwardly from the carpule, through the injection needle and into the patient in response to forwardly directed pressure applied by the user to the plunger piston.

A significant undesirable characteristic of conventional dental needles is that they remain fixed in place throughout a typical dental procedure while awaiting possible further use to administer an additional dose or doses of a medicament such as local anesthesia if the patient begins experiencing pain or discomfort that can be alleviated by the safe administration of additional anesthetic from the same carpule. In many cases, a dentist will simply lay the dental syringe down upon what is thought to be a sterile tray between the serial injections, then pick it up again when another injection is needed, sometimes leading to accidental needle sticks or microbial contamination of the exposed needle between injections. Sometimes dentists will attempt to reapply the original safety cap to the injection needle, thereby risking accidental needle stick injury when the needle is withdrawn from the patient or during the recapping process, and possible resultant contamination and infection by blood-borne pathogens present on the exposed needle.

Recognizing these risk factors, other dental syringes have been disclosed that incorporate various structures and mechanisms that allow the injection needle to be withdrawn coaxially from a forwardly projecting position to a protected position back inside the syringe between injections. Such devices are disclosed, for example, in U.S. Pat. No. 5,997, 512 and in U.S. Pat. No. 6,221,055. However, such devices require modification of the basic conventional dental syringe and cannot be effectuated by simply connecting a frontal attachment to a conventional dental syringe.

SUMMARY OF THE INVENTION

A frontal attachment for a conventional aspirating dental syringe and the combination (or assembly) of the subject frontal attachment with a conventional aspirating dental syringe are disclosed. According to one embodiment of the invention, the frontal attachment desirably comprises a barrel connector housing that is releasably attachable to a mating connector on the front end of the barrel of a conventional aspirating dental syringe. The barrel connector housing desirably further comprises a rearwardly facing carpule needle that is coaxially aligned with the syringe barrel. The frontal attachment also desirably comprises an injection needle guide attached to the barrel connector housing. An injection needle is attached to and supported by a needle holder assembly disposed in oblique relation to the central axis of the aspirating dental syringe. Prior to each successive injection during the procedure, the injection needle is advanced forwardly by applying digital pressure to a touch surface of the needle holder assembly until the injection needle is guided along a needle guide slot into a forwardly projecting position where the injection needle is coaxially aligned with the carpule needle and with the aspirating dental syringe during use. As the injection needle is advanced into coaxial alignment with the dental syringe, a coiled spring surrounding the needle and needle holder is compressed. Once the injection needle and needle holder are guided into coaxial alignment with the carpule needle and carpule, the compressed spring urges the rearwardly facing end of the needle holder into contact with an annular seal seated in the forwardly facing side of the barrel connector housing, thereby reducing the likelihood of unintended fluid leakage from the device during use.

In one embodiment of the invention, the subject frontal attachment comprises a barrel connector housing releasably attachable to the front end of the barrel of an aspirating dental syringe, an injection needle guide attached to the barrel connector housing, an injection needle attached to and supported by a needle holder assembly disposed in a needle guide slot located between the injection needle guide and the barrel connector housing in oblique relation to the longitudinal axis of the aspirating dental syringe, and a rearwardly facing second needle coaxially aligned with and configured to penetrate an elastomeric septum or other liquid barrier disposed in the front end of a carpule inserted into the aspirating dental syringe. In one embodiment, an annular fluid seal is disposed between the injection needle and the rearwardly facing second needle whenever the injection needle is positioned so that fluid communication is established between the injection needle and a carpule disposed in the aspirating dental syringe.

Between uses, or at the conclusion of the procedure, the injection needle is moved to a protected position back inside the frontal attachment by a gentle application of digital pressure to the touch pad in cooperation with the spring force exerted on the needle holder by the expanding coil spring as the needle holder travels obliquely away from the central axis of the syringe along the needle guide slot disposed between the injection needle guide and the barrel connector housing. According to one embodiment of the invention, the needle guide slot is maintained in a desired juxtaposition to the barrel connector housing by a needle guide latch and by a connector housing latch that are each engageable with a cooperating latch capture housing, as described in greater detail below in relation to one satisfactory embodiment of the invention. At the conclusion of the procedure, and with the injection needle withdrawn sufficiently that the needle tip no long projects forwardly from the frontal attachment so as to create a potential hazard to the user, patient or other nearby personnel, the frontal attachment is desirably detached from the syringe (as by unthreading) at the conclusion of the procedure and safely deposited in a receptacle suitable for use with sharps and other potentially hazardous medical waste.

BRIEF DESCRIPTION OF THE DRAWINGS

The apparatus of the invention is further described and explained in relation to the following drawings wherein:

FIG. 7 is a top plan view of the apparatus as in FIGS. 1 and 3, but with the textured touch surface moved forwardly and laterally along the needle guide slot and with the injection needle projecting forwardly in the use position and in fluid communication with the carpule; and FIG. 8 is a cross-sectional top plan view of the apparatus as in FIG. 7.

DESCRIPTION OF A PREFERRED EMBODIMENT

Figure 1:
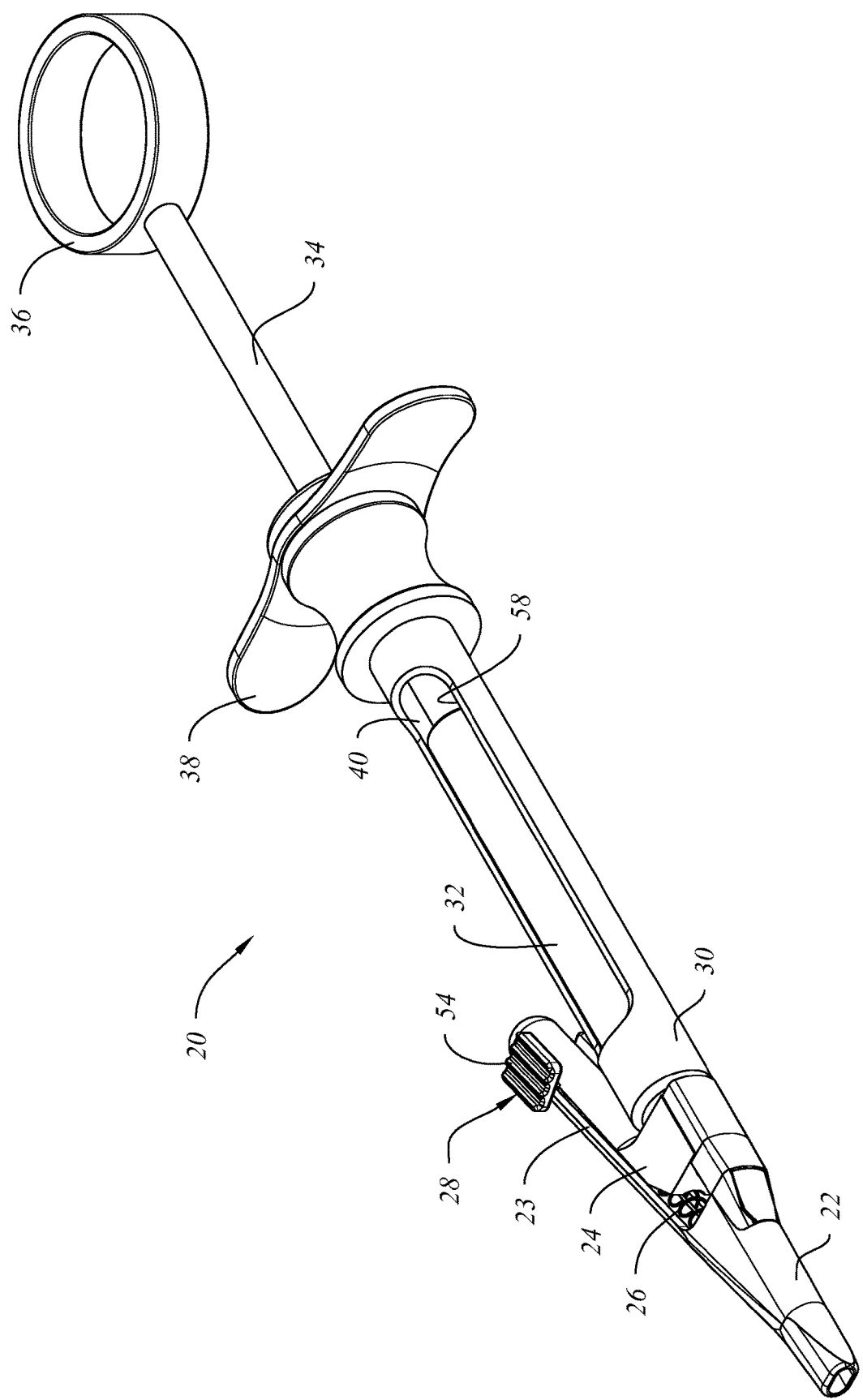
FIG. 1 is a top front perspective view of one satisfactory embodiment of the frontal attachment of the invention as installed on a conventional dental syringe containing a carpule of medicament, wherein the injection needle is withdrawn into the body of the frontal attachment so that the injection needle tip is not projecting from the front of the device.
Figure 2:
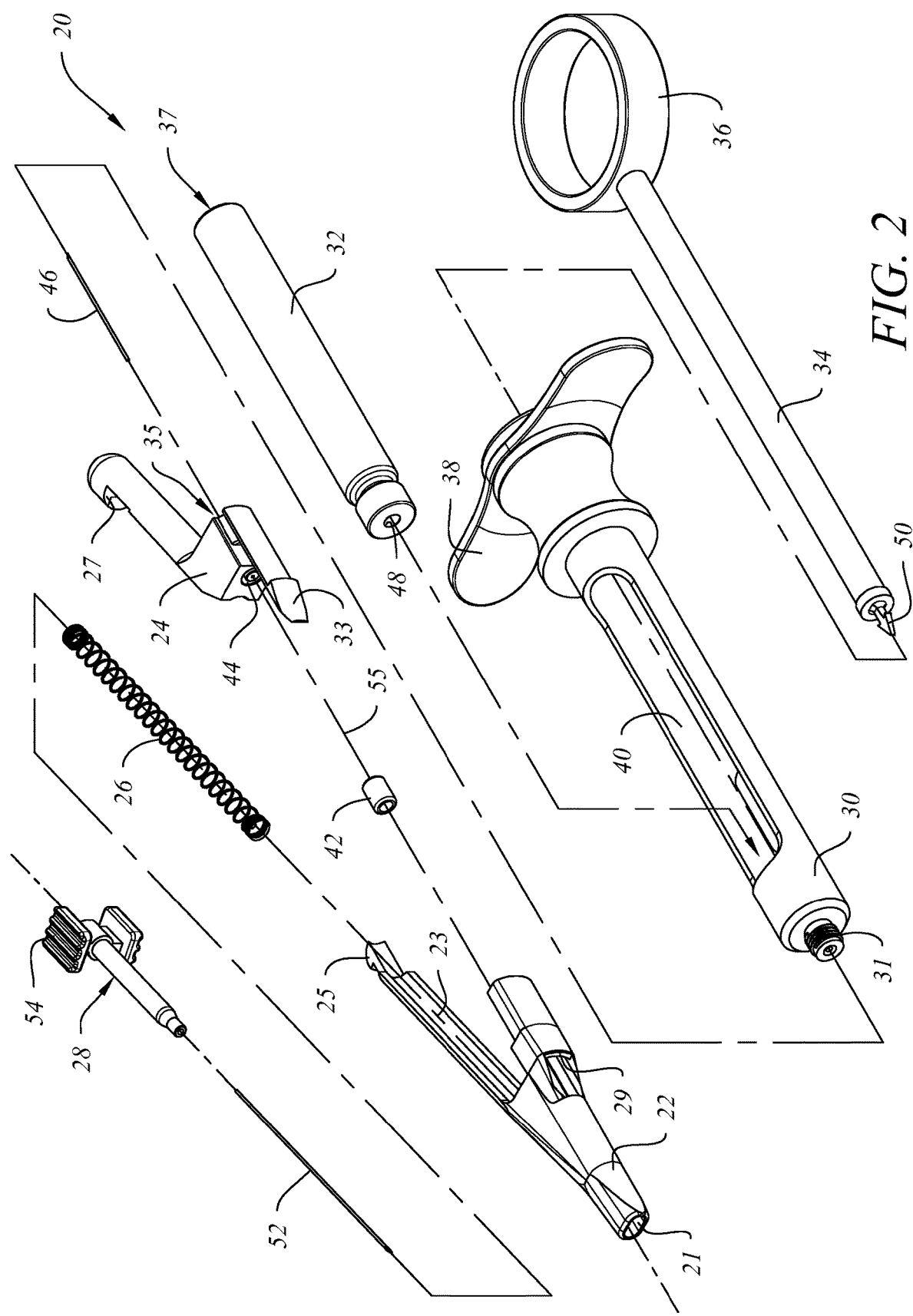
FIG. 2 is an exploded representation of the apparatus as depicted in FIG. 1.
Figure 3:
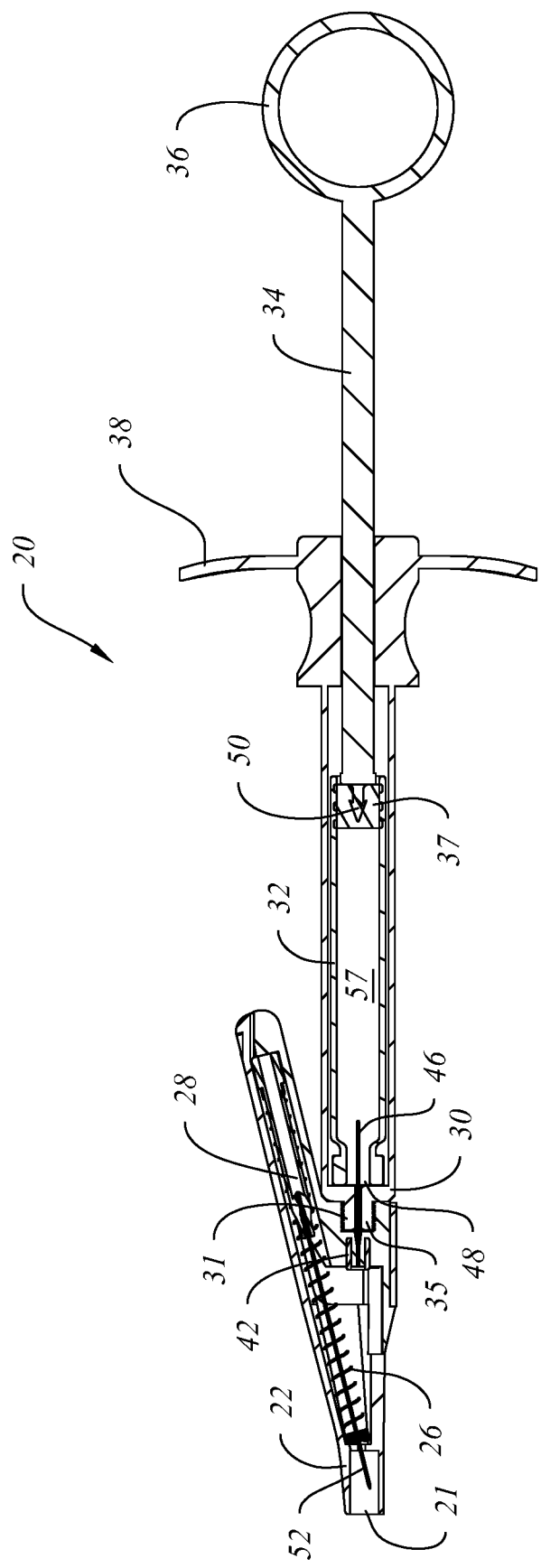
FIG. 3 is cross-sectional top plan view of the apparatus as depicted in FIG. 1.

Referring to FIGS. 1-3, in one embodiment of the invention, aspirating dental syringe assembly 20 is disclosed that comprises a frontal attachment that is releasably connected to syringe connector 31 of barrel 30 of an aspirating dental syringe. The frontal attachment further comprises injection needle guide 22 and barrel connector housing 24 that are cooperatively engageable to define a needle guide slot 23 between them. Syringe connector 31 of barrel 30 is depicted as a male threaded connector in FIGS. 2 and 3, in which case a rearwardly facing, cooperatively threaded female receptacle 35 is desirably provided in barrel connector housing 24 of the frontal attachment along longitudinal axis 55 of aspirating dental syringe assembly 20. Similarly, it will be appreciated that barrel 30 could be provided with a female connector and that barrel connector housing 24 would then desirably comprise a cooperatively engageable fitting. Although cooperatively threaded fittings are preferred for use in releasably connecting the frontal attachment to barrel 30, it will likewise be appreciated that other functionally similar connectors such as, for example, a bayonet-type connector, can also be used. Needle guide slot 23 is desirably disposed in oblique but intersecting relation to longitudinal axis 55 through aspirating dental syringe assembly 20 and is desirably configured to receive and retain injection needle holder assembly 28 in sliding engagement with injection needle guide 22 and barrel connector housing 24.

Injection needle guide 22 further comprises needle guide latch 25 that is insertable into engagement with latch capture element 27 of barrel connector housing 24, and barrel connector housing 24 further comprises barrel connector latch 33 that is insertable into engagement with latch capture element 29. When injection needle guide 22 and barrel connector housing 24 are assembled to define needle guide slot 23 between them, one or more touch surfaces 54 face outwardly from the guide slot so as to be accessible to a user of the device to impart sliding movement to needle holder assembly 28 in either a forward or rearward direction that is oblique in relation to longitudinal axis 55 through the device. Injection needle guide 22, barrel connector housing 24 and injection needle holder assembly 28 are each satisfactorily made of a moldable polymeric material that is suitable for use in such applications.

Prior to assembling injection needle guide 22 and barrel connector housing 24, injection needle 52 and coiled spring 26 are desirably coaxially aligned with a forwardly extending tubular portion of needle holder assembly 28 and coiled spring 26 is seated inside the forwardly extending portion of injection needle guide 22. The rearwardly facing end portion of needle 52 is desirably secured inside the forwardly extending tubular portion of needle holder assembly 28 by gluing or another similarly effective means to hold injection needle 28 in fixed coaxial relation to the tubular portion of needle holder assembly 28. Similarly, the forwardly facing end of rearwardly facing carpule needle 46 is desirably glued or otherwise secured inside an internal bore through barrel connector housing 24 that is coaxially alignable with longitudinal axis 55 and with syringe connector 31 of barrel 30. Prior to aligning and engaging the respective latches 25, 33 and latch capture elements 27, 29 connecting injection needle guide 22 to barrel connector housing 24, annular fluid seal 42 is also desirably inserted into abutting contact with the forwardly facing annular seating surface 44 disposed in the front portion of barrel connector housing 24.

Referring to FIGS. 1 and 3, whenever touch surface 54 of injection needle holder assembly 28 is in its rearmost position relative to injection needle guide slot 23, coiled spring 26 remains in an expanded or slightly compressed position and the forwardly extending tip of needle 52 remains disposed inside front opening 21 of injection needle guide 22. Carpule 32 is disposed inside barrel cavity 40 of the aspirating dental syringe, having been inserted through window 58 of barrel 30. Plunger rod 34 and thumb ring 36 have been advanced sufficiently forward in barrel 30 that barb 50 has engaged stopper 37 at the rear end of carpule 32, and rearwardly facing carpule needle 46 has penetrated elastomeric septum 48 in preparation for injecting fluid, typically although not necessarily a local anesthetic, from interior cavity 57 of carpule 32. At the point shown in FIG. 3, no medicament has been administered to the patient because injection needle is still positioned obliquely relative to the fluid flow path through rearwardly facing carpule needle 46.

Figure 4:
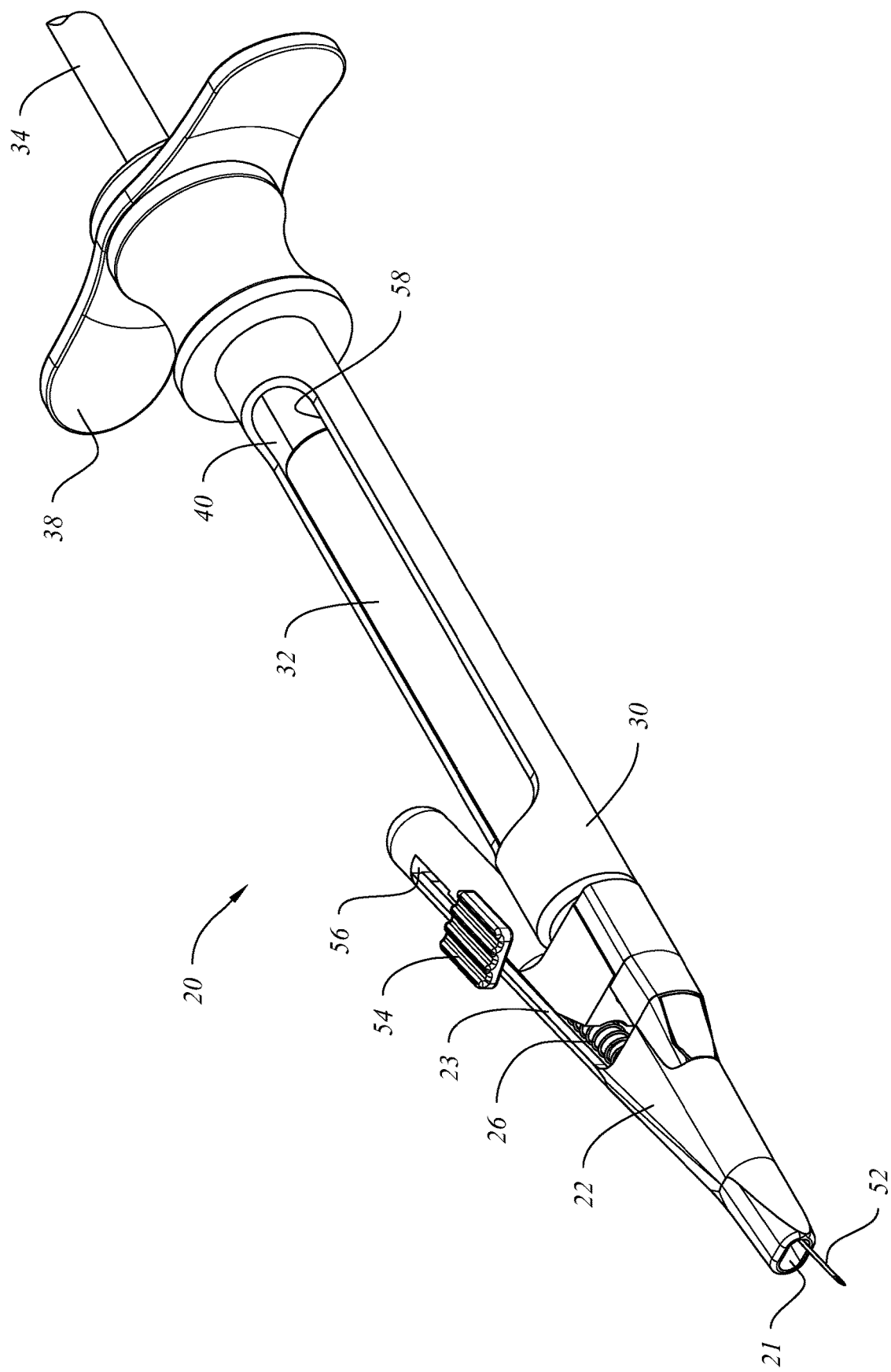
FIG. 4 is a top front perspective view as in FIG. 1 that is slightly enlarged, and wherein a rearwardly extending portion of the plunger rod and the thumb ring are broken away and the textured touch surface of the injection needle holder is advanced forwardly through the needle guide slot a distance sufficient to cause a small portion of the injection needle to project obliquely through the front opening of the needle alignment guide.
Figure 5:
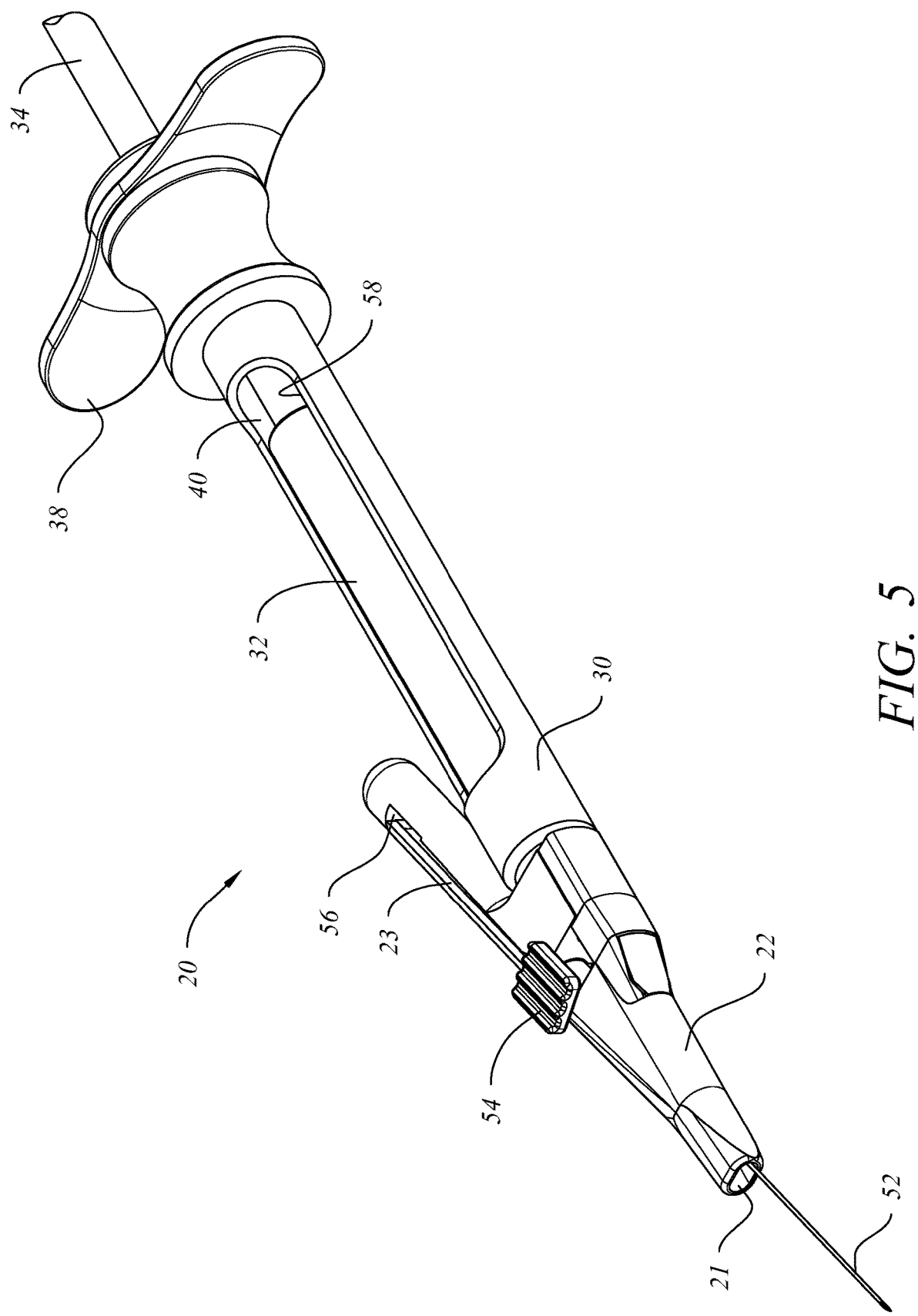
FIG. 5 is a top front perspective view as in FIG. 4 except that the textured touch surface of the injection needle holder is further advanced forwardly through the needle guide slot a distance sufficient to cause most of the injection needle to project obliquely through the front opening of the needle alignment guide.
Figure 6:
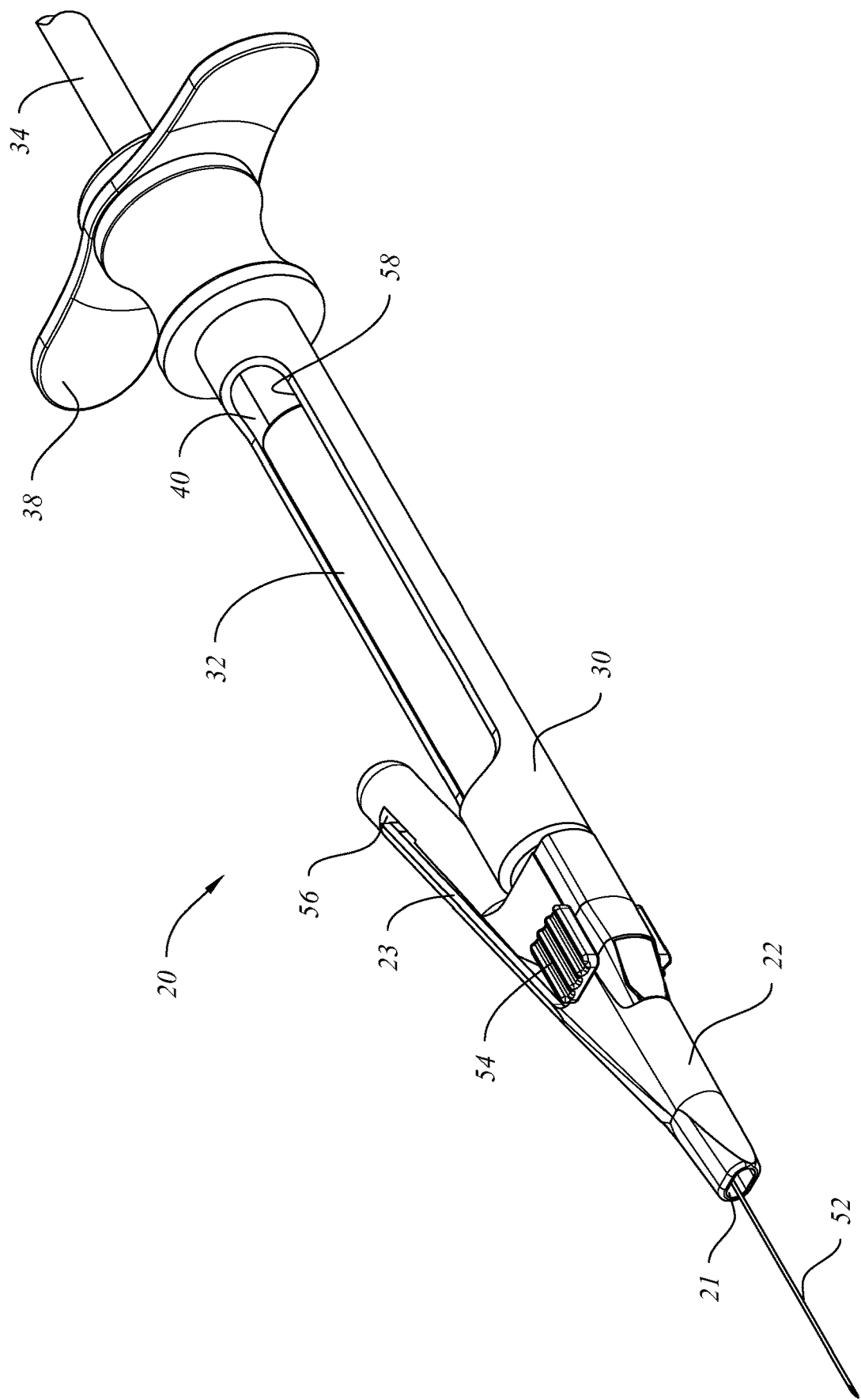
FIG. 6 is a top front perspective view as in FIG. 5 except that the textured touch surface of the injection needle holder is moved laterally within the needle guide slot a distance sufficient to permit the injection needle to project forwardly through the front opening of the needle alignment guide so that it is substantially coaxially aligned with the central axis through the aspirating dental syringe.

Referring to FIGS. 4-5, as manual pressure is applied to touch surface 54, touch surface 54 begins to move forwardly along the incline of needle guide slot 23 and the forwardly extending tip of injection needle 52 begins to project through front opening 21 of needle injection guide 22. It should be noted that front opening 21 is depicted as being slightly elongated in the horizontal direction to accommodate the oblique angle between needle 52 and longitudinal axis 55 (FIG. 2) of barrel 30. When touch surface reaches the position shown in FIG. 5, the curvature of needle guide slot 23 causes touch surface 54 to be repositioned laterally, as seen in FIGS. 6 and 7, to a position where injection needle 52 becomes coaxially aligned with annular fluid seal 42, rearwardly facing carpule needle 46 and longitudinal axis 55 (FIG. 2) through aspirating dental syringe assembly 20. When touch surface 54 reaches the position shown in FIGS. 7 and 8, manual pressure applied by the user to plunger rod 34 through thumb ring 36 and opposed finger flanges 38 causes plunger rod 34 to force stopper 37 forwardly inside carpule 32 and forces the medicament contained inside cavity 57 of carpule 32 to flow forwardly through a fluid flow path defined by rearwardly facing carpule needle 46, annular fluid seal 42, the tubular portion of needle holder assembly 28 and injection needle 52 into a patient.

Following administration of a suitable amount of the local anesthetic or other medicament into the patient for that stage of the dental procedure being performed, injection needle 52 can be withdrawn back inside the protective covering provided by injection needle guide 22 and barrel connector housing 24 of the frontal attachment until such time as another injection may be needed during the same procedure. As injection needle holder 28 is being advanced from the position of FIG. 3 to the position of FIGS. 7-8, coiled spring 26 (FIG. 3) is compressed by the manual force applied through touch surface 54, and when injection needle 52 is coaxially aligned with rearwardly facing carpule needle 46, the compresses coil spring urges the larger diameter head portion of needle holder assembly 28 against annular fluid seal 42, thereby avoiding fluid leakage between injection needle guide 23 and barrel connector housing 24. The, when the forward motion of plunger 34 stops following the initial injection, coiled spring 26 can again expand to a more relaxed position as needle holder assembly 28 moves obliquely along needle guide slot 23. This forward advancement and subsequent retraction of injection needle 52 caused by the reciprocating sequential movement of injection needle holder assembly 28 of the frontal attachment relative to barrel 30 of the aspirating dental syringe can then be continued as needed until completion of the dental procedure, after which the entire frontal attachment and can be safely detached from the dental syringe and deposited into a suitable medical refuse container.

Other alterations and modifications of the invention will likewise become apparent to those of ordinary skill in the art upon reading this specification in view of the accompanying drawings, and it is intended that the scope of the invention disclosed herein be limited only by the broadest interpretation of the appended claims to which the inventors and/or Applicants are legally entitled.

What is claimed is:

1. A frontal attachment for an aspirating dental syringe, the frontal attachment comprising:
   a barrel connector housing releasably attachable to a front end of a barrel of the aspirating dental syringe having a longitudinal axis;
   an injection needle guide attached to the barrel connector housing;
   an injection needle attached to and supported by a needle holder assembly disposed in a slot between the injection needle guide and the barrel connector housing in oblique relation to the longitudinal axis of the aspirating dental syringe; and
   a rearwardly projecting second needle coaxially aligned with and configured to penetrate an elastomeric septum or other liquid barrier disposed in a front end of a carpule inserted into the aspirating dental syringe;
   wherein the needle holder assembly is configured to be reciprocated between a first position in which the injection needle is unexposed and oriented in oblique relation to the longitudinal axis of the aspirating dental syringe, and a second position wherein the injection needle projects forwardly from an opening in the injection needle guide and is coaxially aligned with and in fluid communication with the rearwardly projecting second needle.

2. The frontal attachment of claim 1 further comprising an annular seal disposed between the barrel connector housing and the injection needle guide.

3. The frontal attachment of claim 1 further comprising a coiled spring disposed around a portion of the needle holder assembly.

4. The frontal attachment of claim 3 wherein the coiled spring is not compressed when the needle holder assembly is in the first position.

5. The frontal attachment of claim 3 wherein the coiled spring is compressed when the needle holder assembly is in the second position.

6. The frontal attachment of claim 5 wherein the needle holder assembly further comprises a touch surface through which pressure can be manually applied to move the needle holder assembly selectively from the first position to the second position and from the second position to the first position.

7. The frontal attachment of claim 6 wherein the compressed coiled spring, the needle holder assembly and the slot are cooperatively configured to withdraw the injection needle back inside the injection needle guide upon the further manual application of pressure to the touch surface in a direction oblique to the longitudinal axis of the aspirating dental syringe, thereby causing the needle holder assembly to move from the second position back to the first position and causing the injection needle to be retracted back into a protected position inside the injection needle guide.

8. The frontal attachment of claim 5 wherein the coiled spring biases the needle holder assembly rearwardly against an annular seal disposed between the barrel connector housing and the injection needle guide when the needle holder assembly is disposed in the second position.

9. The frontal attachment of claim 1 wherein the injection needle guide and the barrel connector housing are attached by frictional engagement.

10. The frontal attachment of claim 9 wherein the injection needle guide further comprises a needle guide latch and a first latch capture element.

11. The frontal attachment of claim 9 wherein the barrel connector housing comprises a barrel connector latch and a second latch capture element.

12. The frontal attachment of claim 1 wherein the barrel connector housing further comprises a threaded female receptacle that is releasably attachable to the front end of the barrel.

13. The frontal attachment of claim 12 wherein the rearwardly projecting second needle projects rearwardly through the threaded female receptacle and is coaxially aligned with the injection needle and with the longitudinal axis of the aspirating dental syringe when the needle holder assembly is disposed in the second position.

14. The frontal attachment of claim 1 in combination with an aspirating dental syringe.

\* \* \* \* \*